United States Patent [19]

Adelberg

[11] 4,013,263
[45] Mar. 22, 1977

[54] CLAMP FOR REGULATING FLUID FLOW THROUGH PLASTIC TUBING

[76] Inventor: Marvin Adelberg, 4043 Cody Road, Sherman Oaks, Calif. 91403

[22] Filed: Dec. 24, 1975

[21] Appl. No.: 644,166

[52] U.S. Cl. ..................................... 251/6; 251/7
[51] Int. Cl.² .......................................... F16K 7/06
[58] Field of Search ............................. 251/4, 6–10

[56] References Cited

UNITED STATES PATENTS

| | | | |
|---|---|---|---|
| 3,477,686 | 11/1969 | Engelsher et al. .................. | 251/10 |
| 3,685,787 | 8/1972 | Adelberg ............................. | 251/6 |

*Primary Examiner*—Martin P. Schwadron
*Assistant Examiner*—Richard Gerard
*Attorney, Agent, or Firm*—Edward A. Sokolski

[57] ABSTRACT

Tubing through which fluid flow is to be regulated is placed in a regulating clamp wherein it is clamped between a roller wheel and a surface having a variable cross-sectional area channel extending therealong. This surface is parallel to the travel path of the wheel, and thus there is a constant separation distance between these two elements for all wheel positions. Flow rate through the tubing is changed by longitudinal adjustment of the position of the roller wheel, the ratio of the portion of the tubing which is clamped between the wheel and the surface to that which is not clamped and over the channel, thereby being varied. A plurality of ridge elements are formed in the surface and act to locally pinch or grip the tubing at discrete intervals, thereby substantially lessening creep of the plastic tubing which, in turn, minimizes the flow rate change once the clamp has been set for the desired rate of flow.

8 Claims, 8 Drawing Figures

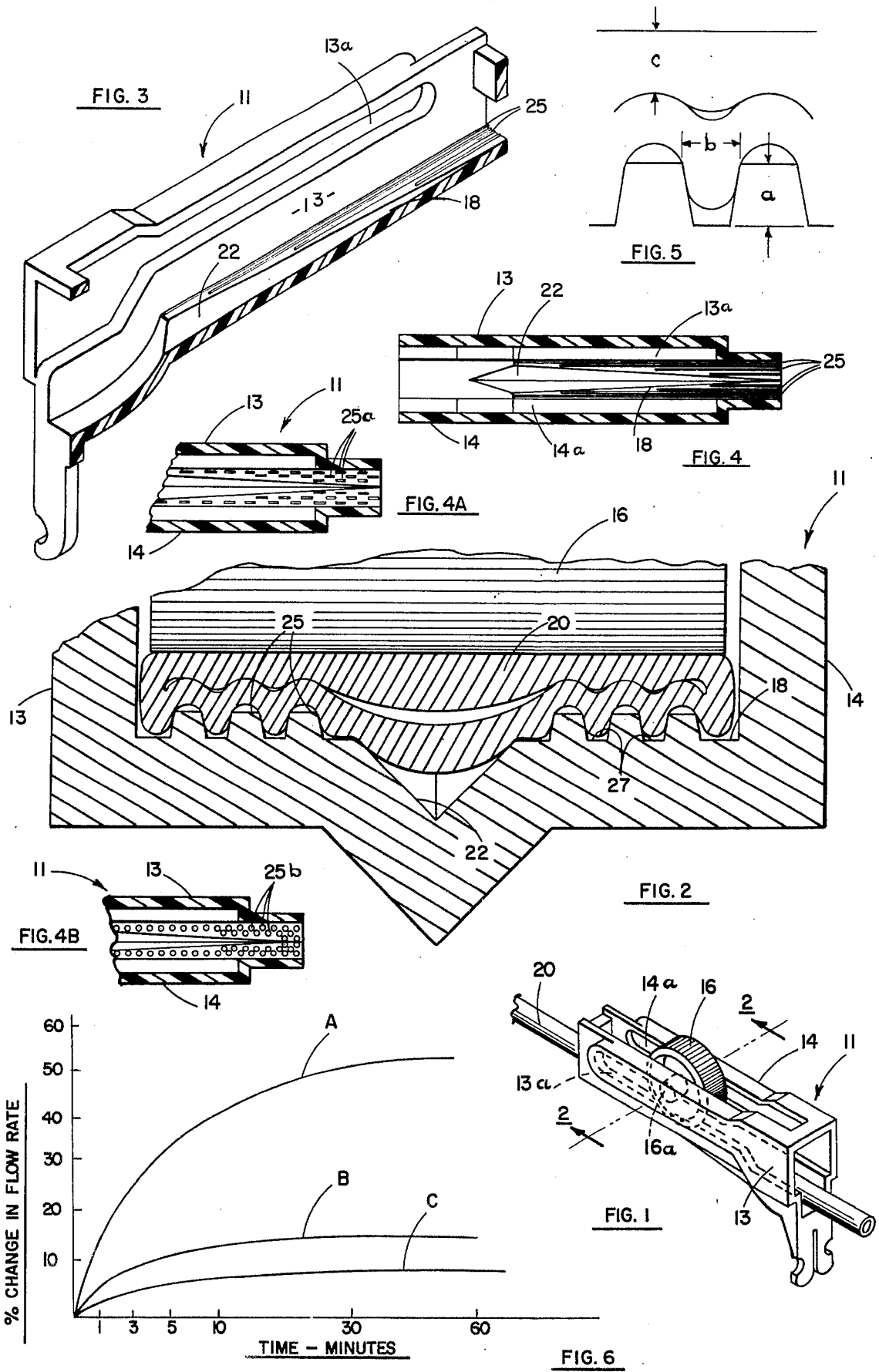

CLAMP FOR REGULATING FLUID FLOW THROUGH PLASTIC TUBING

This invention relates to clamp devices for use in regulating fluid flow through plastic tubing, and more particularly to such a device utilizing a roller wheel which is longitudinally adjusted relative to a surface having a variable cross-section channel, to adjust and set the flow rate.

The maintenance of a constant flow rate through a tube is particularly important in administering intravenous infusions. In my U.S. Pat. No. 3,685,787, a roller clamp device for use in regulating fluid flow through plastic tubing is described which is particularly suited for this purpose. This device has been found to exhibit vast improvement in the constancy of flow rate it provides as compared with prior art devices. There is, however, still some small variation in flow rate in this patented device which is significant enough to cause concern. This is due to a small amount of creep or "cold flow" of the plastic tubing material (usually polyvinylchloride) which is soft and essentially incompressible. It has been found that very small deviations in the flow passage geometry can account for relatively larger changes in the flow rate. It is estimated that for every 1% change in effective tube flow cross-section, a change in the flow rate of about 4% can be expected.

The present invention provides an improvement over the device of my aforementioned patent by lessening creep of the plastic tubing material, thereby making for an even less varying flow rate. This end result is achieved by providing means along the clamping surface of the clamp for pinching or gripping the tubing at discrete locations or intervals so as to confine small segments of the tubing between the pinching elements. Hence, although nearly the percent creep (expressed as a percentage of some reference length) may still exist, the magnitude of creep (not expressed as a percentage) will be significantly reduced.

It is therefore an object of this invention to reduce the variations in flow rate in the administration of intravenous infusions.

It is a further object of this invention to provide an improved clamp for regulating fluid flow through plastic tubing wherein the creep of the tubing is lessened.

Other objects of this invention will become apparent as the description proceeds in connection with the accompanying drawings, of which:

FIG. 1 is a perspective drawing of a preferred embodiment of the invention;

FIG. 2 is a portion of a cross-sectional view taken along the plane indicated by 2—2 in FIG. 1;

FIG. 3 is a perspective view with a cut-away section of the body portion of the preferred embodiment;

FIG. 4 is a cross-sectional view illustrating the clamping surface of the preferred embodiment;

FIG. 4A is a cross-sectional view illustrating an alternative form for the clamping surface;

FIG. 4B is a cross-sectional view illustrating still another form for the clamping surface;

FIG. 5 is a schematic view illustrating the ridge structure of the preferred embodiment; and FIG. 6 is a graph illustrating the improved operation afforded by the device of the invention.

Briefly described, the device of the invention is as follows: A flow regulating clamp of the type described in my U.S. Pat. No. 3,685,787 has a body portion with a longitudinal clamping surface. This clamping surface has a variable cross-section longitudinal channel formed therein. A roller wheel is mounted in the body for longitudinal motion parallel to the clamping surface, there being a constant clearance distance between the roller wheel and the clamping surface with motion of the wheel. Plastic tubing is clamped between the roller wheel and the clamping surface, the flow cross-sectional area of the tubing being adjusted in accordance with positioning of the wheel. A plurality of raised portions, which are separated from each other by discrete valley portions, are formed in the clamping surface to locally pinch or grip the tubing at discrete locations or intervals, thereby substantially lessening creep of the plastic and minimizing flow rate change once the clamp has been set for the desired rate of flow. In the preferred embodiment, the raised portions or elements are in the form of long ridges which are spaced from each other so as to constrain the tubing in an optimum manner for reduction of creep.

Referring now to FIGS. 1–5, a preferred embodiment of the invention is illustrated. The clamp has a body portion or housing 11 having side walls 13 and 14 with oppositely positioned trunnion grooves 13a and 14a formed therein. Roller wheel 16 has a pair of trunnions (one of which, 16a, is shown in FIG. 1) extending therefrom which ride in grooves 13a and 14a respectively. The body also has a bottom surface 18 which serves as a clamping surface against which plastic tubing 20 is clamped by wheel 16. Formed in the central part of surface 18 is variable width and variable depth channel 22. Clamping surface 18 is parallel to grooves 13a and 14a such that the separation distance between wheel 16 and surface 18 remains constant throughout the travel of the wheel on its trunnions. The flow rate of fluid through tubing 20 is adjusted to the desired value by positioning wheel 16 along grooves 13a and 14a, whereby the tubing is compressed against surfaces which are adjacent to different portions of the channel which has varying depths and widths. The device as thus far described is identical to the preferred embodiment of that of my aforementioned U.S. Pat. No. 3,685,787, and reference to that patent may be made for additional descriptive details of the structure and operation of the device as thus far described.

The present invention is involved with the addition of a plurality of elements, ridges or raised portions 25 formed in surface 18. Raised portions 25 are separated from each other by discrete valley portions 27. In the preferred embodiment, ridges 25 are made substantially parallel to the longitudinal axis of the body to facilitate manufacturing; however, they could also run in other directions and/or be a series of interrupted elements or ridges of equal or unequal length. Referring now to FIG. 5, for minimum creep, the height "$a$" of ridges 25 and the spacing "$b$" between ridges are preferably made substantially equal to each other and to the compressed wall thickness, "$c$", of the tubing. Where polyvinylchloride tubing is utilized, the tubing wall, when compressed against surface 18 by wheel 16, generally is reduced to a thickness of about one-half of its nominal uncompressed thickness. In an operative embodiment of the invention utilizing a polyvinylchloride tubing having a nominal wall thickness of 0.020 inches and an estimated compressed wall thickness of some 0.010 inches, ridges having a height and spacing of 0.008 inches were used, and produced the improvement in flow rate stability described further on in the specification in connection with FIG. 6. The tops of ridges 25 are preferably rounded which will still provide a good grip on the tubing and effectively lessen creep but will not damage the tubing as sharp edged ridges might.

Referring now to FIGS. 4A and 4B, alternative forms for the raised portions of the clamping surface are illustrated. As shown in FIG. 4A, the surface may have a plurality of spaced apart ridge members 25a formed thereon or, as shown in FIG. 4B, the surface may have a plurality of spaced rounded projections 25b to implement the clamping action.

Referring now to FIG. 6, a graph is shown illustrating flow rate variations due to the relative creep characteristics of conventional clamps, clamps made in accordance with my U.S. Pat. No. 3,685,787, and the clamp of the present invention. The graph line marked "A" indicates percent change in flow rate in a prior art conventional clamp. The graph line marked "B" shows the percent change in flow rate with the clamp of my U.S. Pat. No. 3,685,787. The graph line marked "C" indicates the percent change in flow rate with the clamp of the present invention used with the same tubing as for cases "A" and "B" and having a nominal wall thickness of 0.020 inches (compressed wall thickness of 0.010 inches) and ridges having both a height, "$a$", and spacing, "$b$" (see FIG. 5) of 0.008 inches. It can be seen from this graph that the device of the present invention reduces the change in flow rate substantially as compared with the device of my Pat. No. 3,685,787.

While the invention has been described and illustrated in detail, it is to be clearly understood that this is intended by way of illustration and example only and is not to be taken by way of limitation, the spirit and scope of this invention being limited only by the terms of the following claims.

I claim:

1. In a clamp for regulating fluid flow through plastic tubing having a body portion with a longitudinal clamping surface, a variable cross-section longitudinal channel being formed in or along said surface and a roller wheel mounted in said body for longitudinal motion parallel to said clamping surface, the tubing being clamped between the roller wheel and said surface, the improvement comprising:
a plurality of distributed raised portions separated from each other by discrete valley portions formed in said clamping surface for locally gripping the tubing wall at given locations, the height of said raised portions above the lowest point of said valley portions and the separation between said raised portions having magnitudes of the order of the compressed wall thickness of the tubing, thereby constraining the tubing so as to reduce creep thereof.

2. The clamp of claim 1 wherein said raised portions are in the form of ridges.

3. The clamp of claim 2 wherein said ridges run substantially parallel to each other.

4. The clamp of claim 3 wherein said ridges run substantially parallel to the longitudinal axis of said clamping surface.

5. The clamp of claim 3 wherein the height ($a$) of said ridges and the separation ($b$) between ridges are substantially equal to each other and to the compressed wall thickness ($c$) of the tubing.

6. The clamp of claim 5 wherein the top portions of said ridges are rounded.

7. The clamp of claim 1 wherein said raised portions are in the form of spaced apart ridge members.

8. The clamp of claim 1 wherein said raised portions are in the form of spaced apart rounded projections.

* * * * *